(12) United States Patent
Hassler et al.

(10) Patent No.: US 10,022,517 B2
(45) Date of Patent: Jul. 17, 2018

(54) SYSTEM, AND PROCESS, AND DEVICE FOR EMISSION OR AUGMENTATION OF ENERGY AFFECTING THE HUMAN BODY

(71) Applicants: Richard Michael Hassler, Laconia, NH (US); Michael Gerhard Hassler, Laconia, NH (US); Richard Jack Hassler, Laconia, NH (US)

(72) Inventors: Richard Michael Hassler, Laconia, NH (US); Michael Gerhard Hassler, Laconia, NH (US); Richard Jack Hassler, Laconia, NH (US)

(*) Notice: Subject to any disclaimer, the term of this patent is extended or adjusted under 35 U.S.C. 154(b) by 0 days.

(21) Appl. No.: 15/864,195

(22) Filed: Jan. 8, 2018

(65) Prior Publication Data

US 2018/0126118 A1 May 10, 2018

Related U.S. Application Data

(63) Continuation-in-part of application No. 15/331,600, filed on Oct. 21, 2016, now Pat. No. 9,727,764, which is a continuation-in-part of application No. 14/856,334, filed on Sep. 16, 2015, now Pat. No. 9,895,528, which is a continuation-in-part of application No. 14/670,152, filed on Mar. 26, 2015.

(60) Provisional application No. 61/933,682, filed on Jan. 30, 2014.

(51) Int. Cl.
*A61M 21/02* (2006.01)
*H04B 13/00* (2006.01)
*A61M 21/00* (2006.01)
*A61N 1/04* (2006.01)

(52) U.S. Cl.
CPC ..... *A61M 21/02* (2013.01); *A61M 2021/0011* (2013.01); *A61M 2021/0055* (2013.01); *A61N 1/0456* (2013.01); *H04B 13/005* (2013.01)

(58) Field of Classification Search
CPC .......... A61M 21/02; A61M 2021/0011; A61M 2021/0055; A61N 1/0456; H04B 13/005
See application file for complete search history.

(56) References Cited

U.S. PATENT DOCUMENTS

| 7,825,667 B2 * | 11/2010 | Fang .................... A61B 5/0507 324/637 |
| 2016/0001091 A1 | 1/2016 | Hassler et al. |
| 2016/0285565 A1 | 9/2016 | Hassler et al. |

FOREIGN PATENT DOCUMENTS

WO   WO 2016 057087 A1   4/2016

OTHER PUBLICATIONS

Chrissa Chverchko, "Georgia Inventor Receives Cash Prize and Grand Prix Award at InventHelp's INPEX® 2016, America's Largest Invention Show" PRWeb ebooks, Jun. 16, 2016, Pittsburgh, PA.

* cited by examiner

*Primary Examiner* — Melissa Koval
*Assistant Examiner* — Trung Nguyen
(74) *Attorney, Agent, or Firm* — Plager Schack LLP

(57) ABSTRACT

A chip may be programmed to emit and/or augment energy tuned to interact with bodily functions through transdermal contact. The chip may be programmed by using a pair of Tesla pancake coils, each coupled to a spherical electrode and driven to create an energetic field between the electrodes. Embodiments may include systems that include the programmed chip in a fabric body. The systems may be wearable so that the effects of the programmed chip may be applied to selected areas of the human body. Some embodiments may be useful for augmenting healing of ailments.

6 Claims, 8 Drawing Sheets

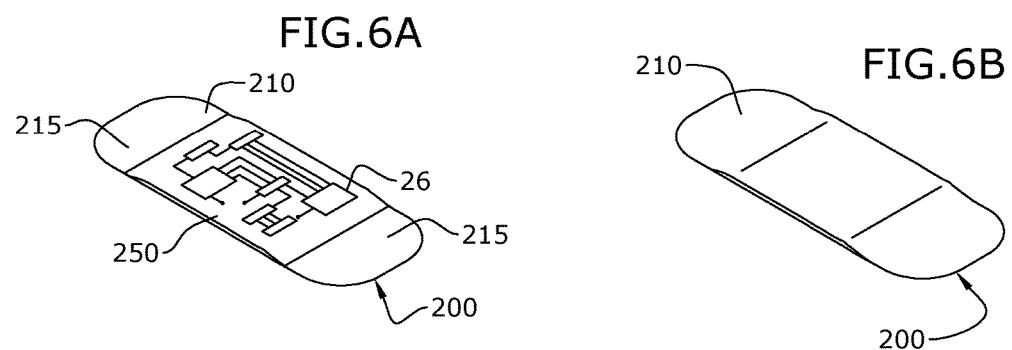
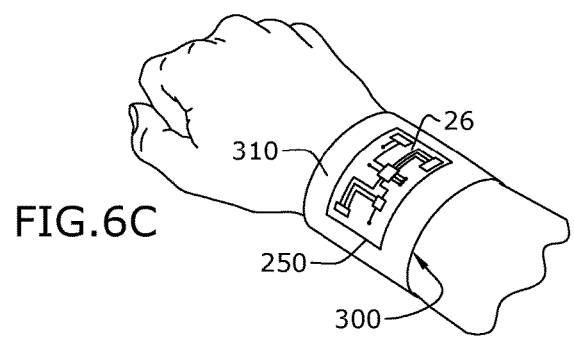
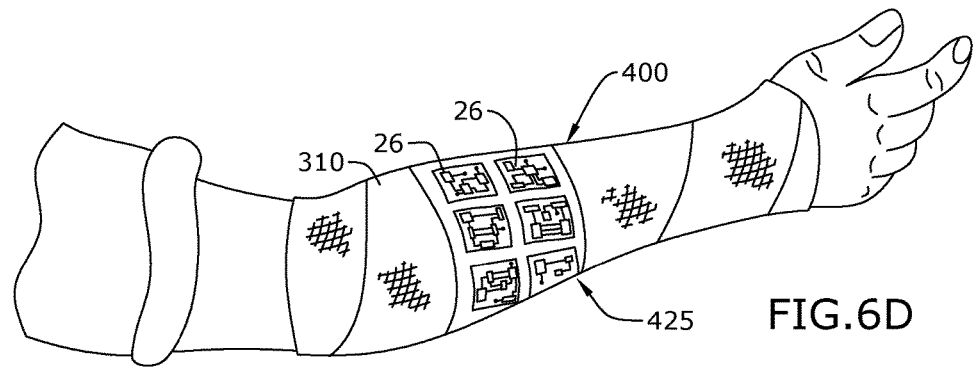

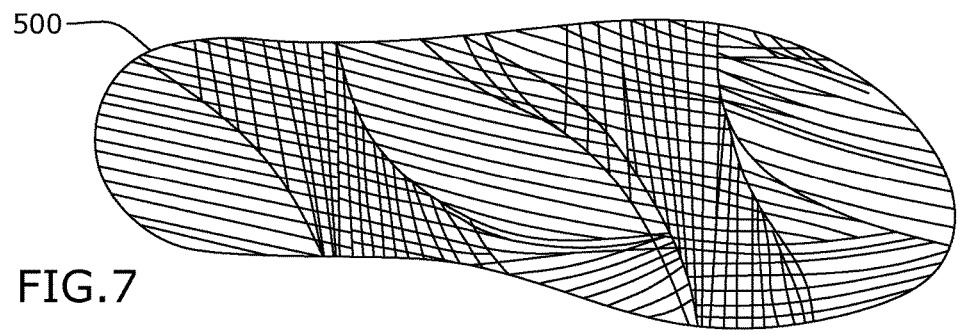
FIG.7
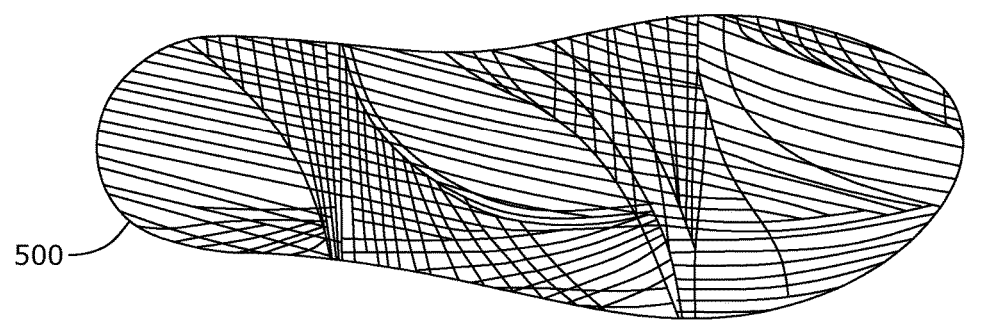
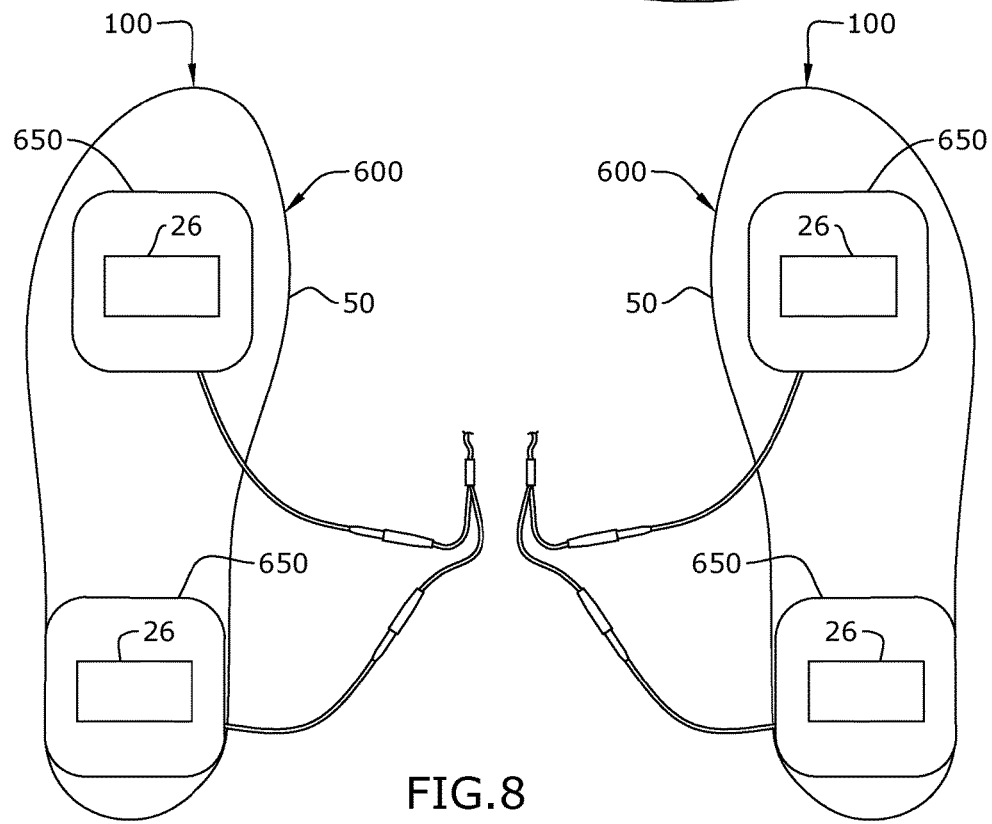
FIG.8

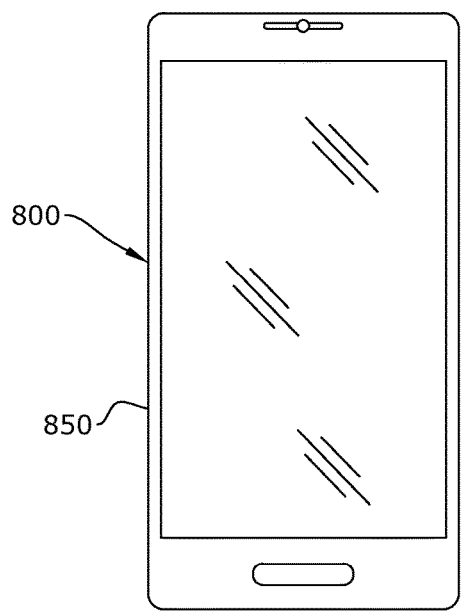
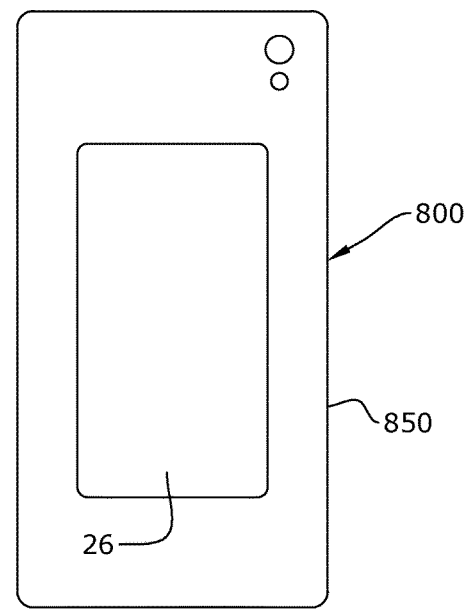
FIG.11A  FIG.11B
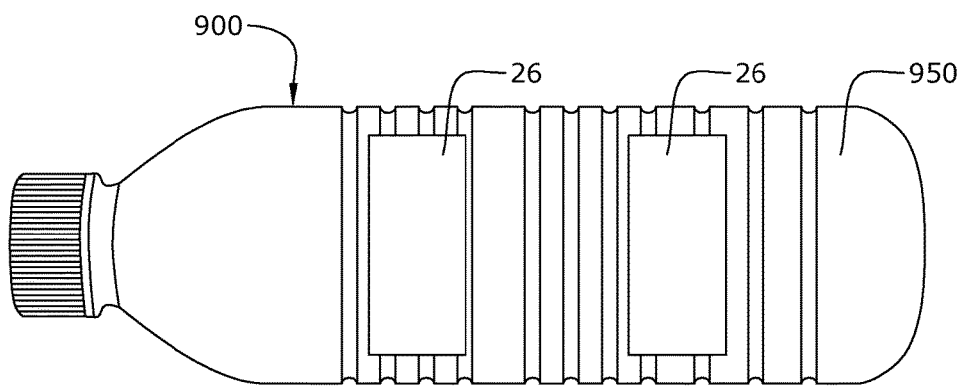
FIG.12

SYSTEM, AND PROCESS, AND DEVICE FOR EMISSION OR AUGMENTATION OF ENERGY AFFECTING THE HUMAN BODY

CROSS-REFERENCE TO RELATED APPLICATIONS

This application claims benefit under 35 U.S.C. § 119(e) of U.S. Provisional Application having Ser. No. 61/933,682 filed Sep. 22, 2014, U.S. Non-Provisional Application having Ser. No. 14/670,152 filed Mar. 26, 2015, U.S. Non-Provisional Application having Ser. No. 14/856,334 filed Sep. 16, 2015, and U.S. Non-Provisional Application having Ser. No. 15/331,600 filed Oct. 21, 2016, which are hereby incorporated by reference herein in its entirety.

BACKGROUND

The embodiments herein relate generally to systems and chips for transdermal emission/augmentation of energy.

The ability to carry information through longitudinal wave carriers has until now, been underutilized. FIG. 1 shows an example of a Tesla coil, waveform/signal generator connected to a spherical electrode as disclosed by Konstantin Meyl's book *Scalar Wave Technology: Documentation for the Experimental-Kit for the Transmission of Electrical Scalar Waves*. Configured correctly, the Tesla coil may produce a longitudinal wave which may carry energetic information over space. FIG. 2 shows a configuration of connections of the components of longitudinal (scalar) electromagnetic wave/field generating equipment with additional connections to different jumper fields as disclosed by Konstantin Meyl. The configuration may transfer a waveform signal from the transmitter side to the receiver side and vice versa via the longitudinal waves carried through the field between two spherical electrodes.

Stressors to the human body have increased tremendously in the past few decades. Genetically modified foods, pollutions, toxins, and other sources have affected the ability of a human body to function in the way it was naturally intended to. The inventions of radio, cellular communication and other such devices that transmit electromagnetic waves/fields have also caused a new kind of stress to the body, electromagnetic pollution. Electromagnetic pollution is electric, magnetic or electromagnetic fields/waves which have a negative effect on health. Electromagnetic pollution is a relatively new kind of stressor to the body that needs to be dealt with. Cell phones and similar EMF emitting devices ex: transponders and GPS locators are a source of electromagnetic pollution and are used by over 90% of adults according to Pew Research Center. Electromagnetic pollution can cause a variety of serious health problems and negative stressors to the body which include: DNA damage, an increased risk of cancer, loss of fertility, effects on brain function, metabolic changes, disruption of the immune system, and thermodynamic changes of the body.

There exist a number of approaches to communicate with the human biofield to produce a desired reaction in the body, which include for example acupuncture as well as a variety of other techniques. Electricity, magnetism, electromagnetic waves/fields, and acoustic waves can all be used to send messages to the body and its energetic field. For example a study done by the department of biomedical engineering at Columbia University found that pulsed electromagnetic field therapy had a significant and rapid impact on pain from early knee osteoarthritis. The human body can be influenced by different forms of electromagnetic waves/fields and frequencies to deal with stressors and illness to the body.

As can be seen, there is a need for a device and system that may positively communicate to the human biofield to combat the negative effects experienced by the human body.

SUMMARY

According to one embodiment of the subject technology, a device for emission of energy comprises a substrate; and a programmable layer of the substrate, wherein: the programmable layer is programmed with longitudinal electromagnetic scalar waves passed through a tuning medium apart from the substrate, the longitudinal electromagnetic scalar waves having an amplitude of the waveform change to modulate desired information onto a carrier wave, electromagnetic waves in the form of light and/or sound are used to modulate the carrier wave as it programs the substrate at either one or any combination of receiving and transmitting pancake coils, and the programmable layer is configured to emit and/or augment energetic information from the substrate, tuned via the longitudinal electromagnetic scalar waves, the energetic information being tuned for interaction with a human body.

BRIEF DESCRIPTION OF THE FIGURES

The detailed description of some embodiments of the present invention is made below with reference to the accompanying figures, wherein like numerals represent corresponding parts of the figures.

FIG. 6A is a perspective top view of a bandage system including a programmed chip of FIG. 4 in accordance with an embodiment of the subject technology;

FIG. 6B is a perspective bottom view of the bandage system of FIG. 6A;

FIG. 6C is a top view of a bandage system including a programmed chip of FIG. 4 attached over a bandage wrapped around a wrist in accordance with an embodiment of the subject technology;

FIG. 6D is a perspective view of a bandage system including an array of programmed chips partially exposed between layers of gauze in accordance with an embodiment of the subject technology;

FIG. 7 is a top view of a pair of insoles comprising respectively programmed chips for transdermal emission of energy in accordance with an embodiment of the subject technology;

FIG. 8 is a bottom view of a pair of insoles including respectively programmed chips for transdermal emission of energy and transcutaneous electrical nerve stimulation units in accordance with an embodiment of the subject technology;

FIGS. 11A and 11B are front and rear views respectively of an electronic mobile device incorporating a programmed chip of FIG. 4 in accordance with an embodiment of the subject technology; and FIG. 12 is a side view of a bottle of fluid incorporating a programmed chip of FIG. 4 in accordance with an embodiment of the subject technology.

DETAILED DESCRIPTION OF CERTAIN EMBODIMENTS

Broadly, embodiments of the subject technology provide a system, method, and product of the system and method that uses information carried by longitudinal waves to program a 'chip' for transdermal emission and/or augmentation of energy. A "chip" may be a hologram, carbon fiber or other programmable substrate. Embodiments of the subject technology have been proven to help the body fight off the negative stressors of electromagnetic pollution and allow the body to function healthier. Aspects of the disclosed chip or substrate produces a positive effect on people and allows the body to function at its optimal rate in the presence of the above described stressors. In a heart rate variable study done by Dr. Joseph Teff the effects of cell phone use with and without the disclosed chip were tested. The results found the chips were effective in reducing stress to the central nervous system caused by the detrimental electromagnetic frequencies from cell phone use. In another study done by Modern Testing Services the thermodynamic effects of cell phone use with and without the disclosed chip was tested. The results were conclusive and found that cell phone use with an embodiment of the disclosed chip on a phone dramatically reduced the thermodynamic stress to the human body caused by cell phone use.

In an exemplary use, the chip may be integrated into a wearable article or may be directly worn by a person. The chip may be programmed to emit and/or augment energetic frequencies/information that are tuned to interact with a bodily function. In an exemplary embodiment, the chip includes a hologram carrying the information. For example, the chip may be tuned to output and/or augment an energetic frequency that causes blood flow to increase/decrease within a portion of the body in proximity to the chip.

The word "exemplary" is used herein to mean "serving as an example or illustration." Any aspect or design described herein as "exemplary" is not necessarily to be construed as preferred or advantageous over other aspects or designs. The word "information" is used herein to refer to a specific frequency or range of frequencies or waveforms emitted by an object in the form of an electromagnetic wave or field. The word "augment" is used herein to refer to interacting with the charge or field of another object.

Figure 1:
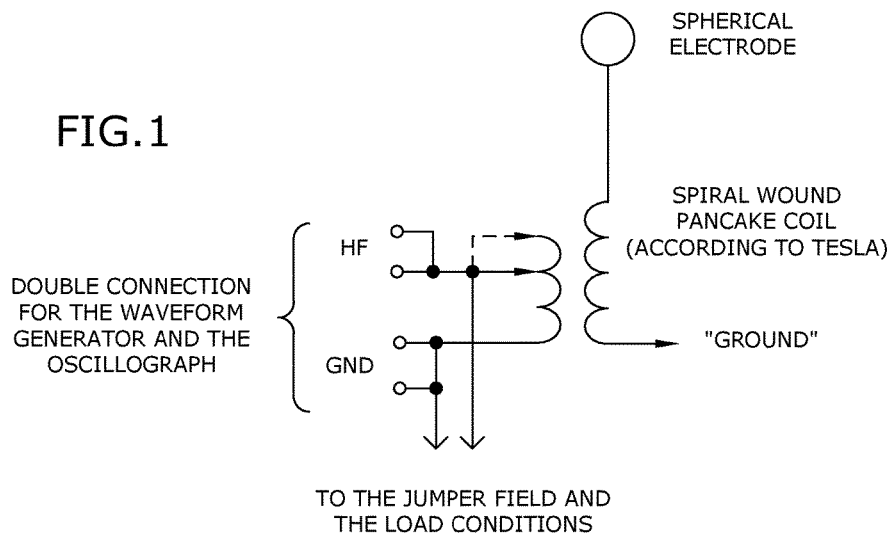
FIG. 1 is a schematic of an air cored transformer with couple coil and pancake coil.
Figure 3:
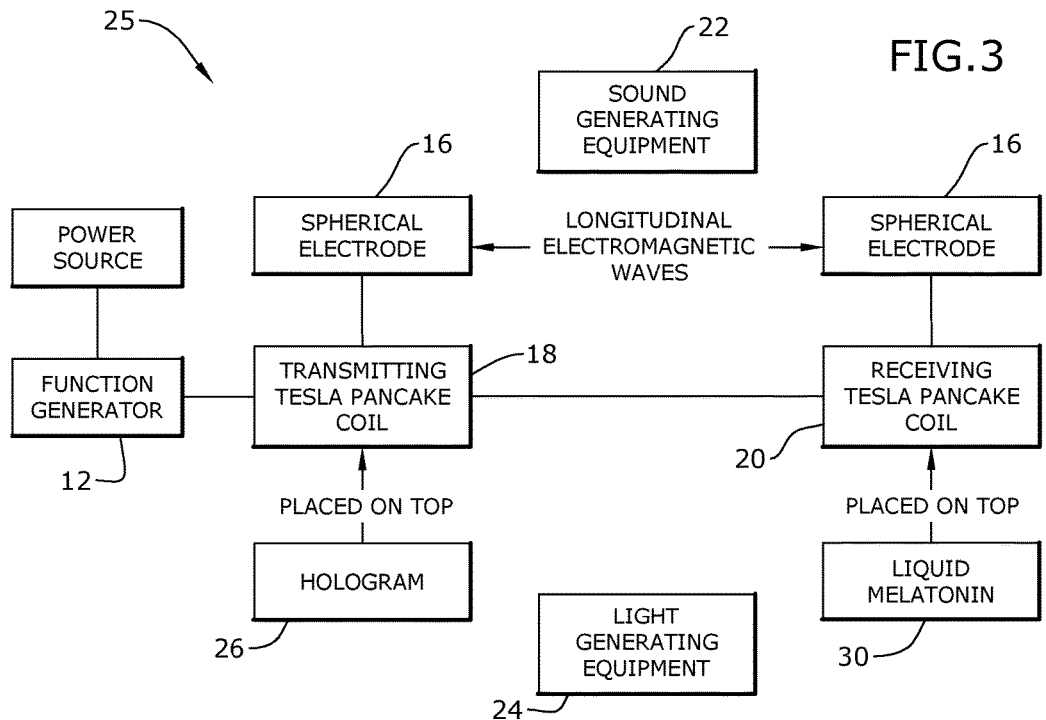
FIG. 3 is a block diagram of a system for programming a chip for transdermal emission of energy in accordance with an embodiment of the subject technology.
Figure 2:
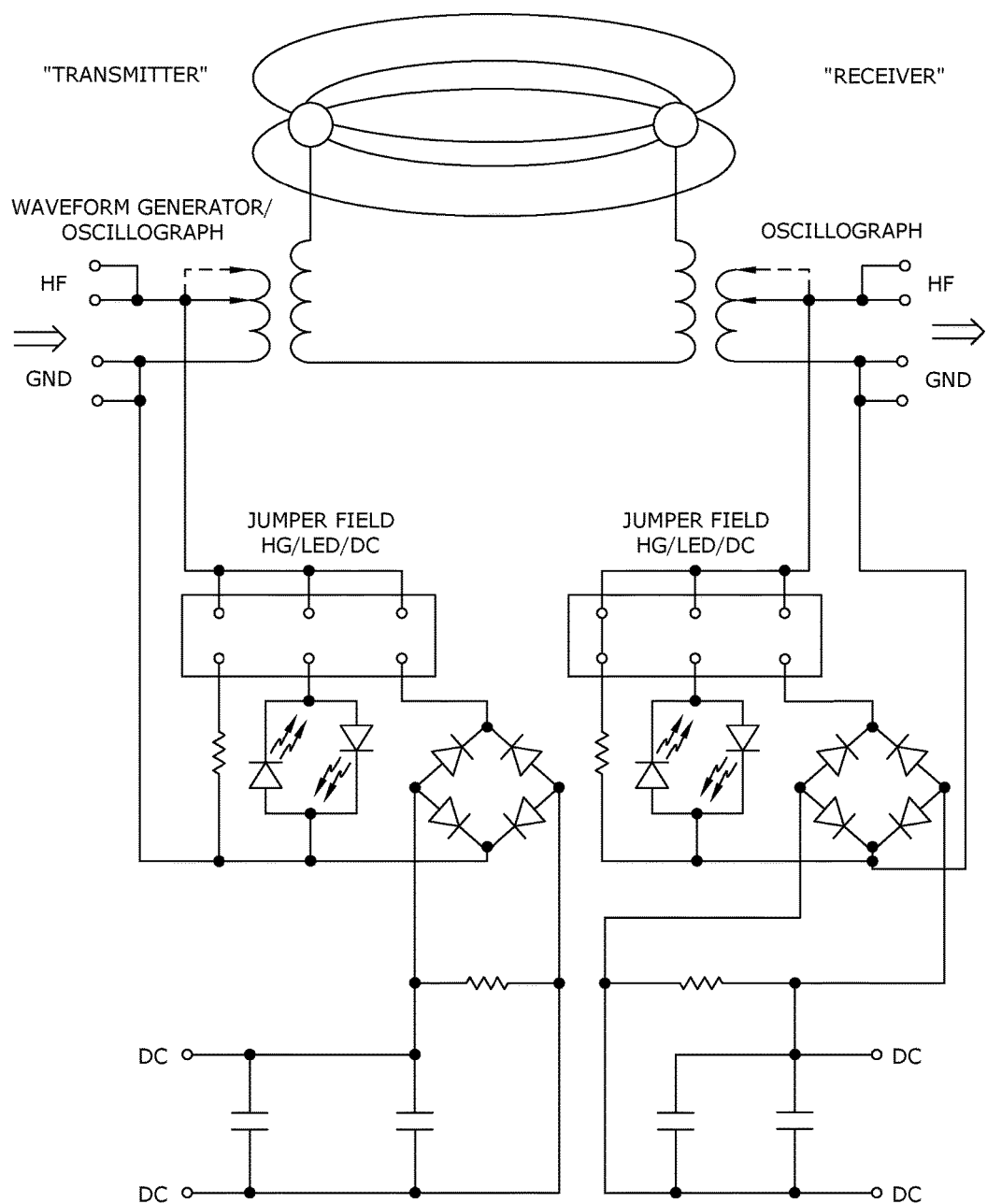
FIG. 2 is a schematic of a longitudinal wave/field generating circuit.
Figure 4:
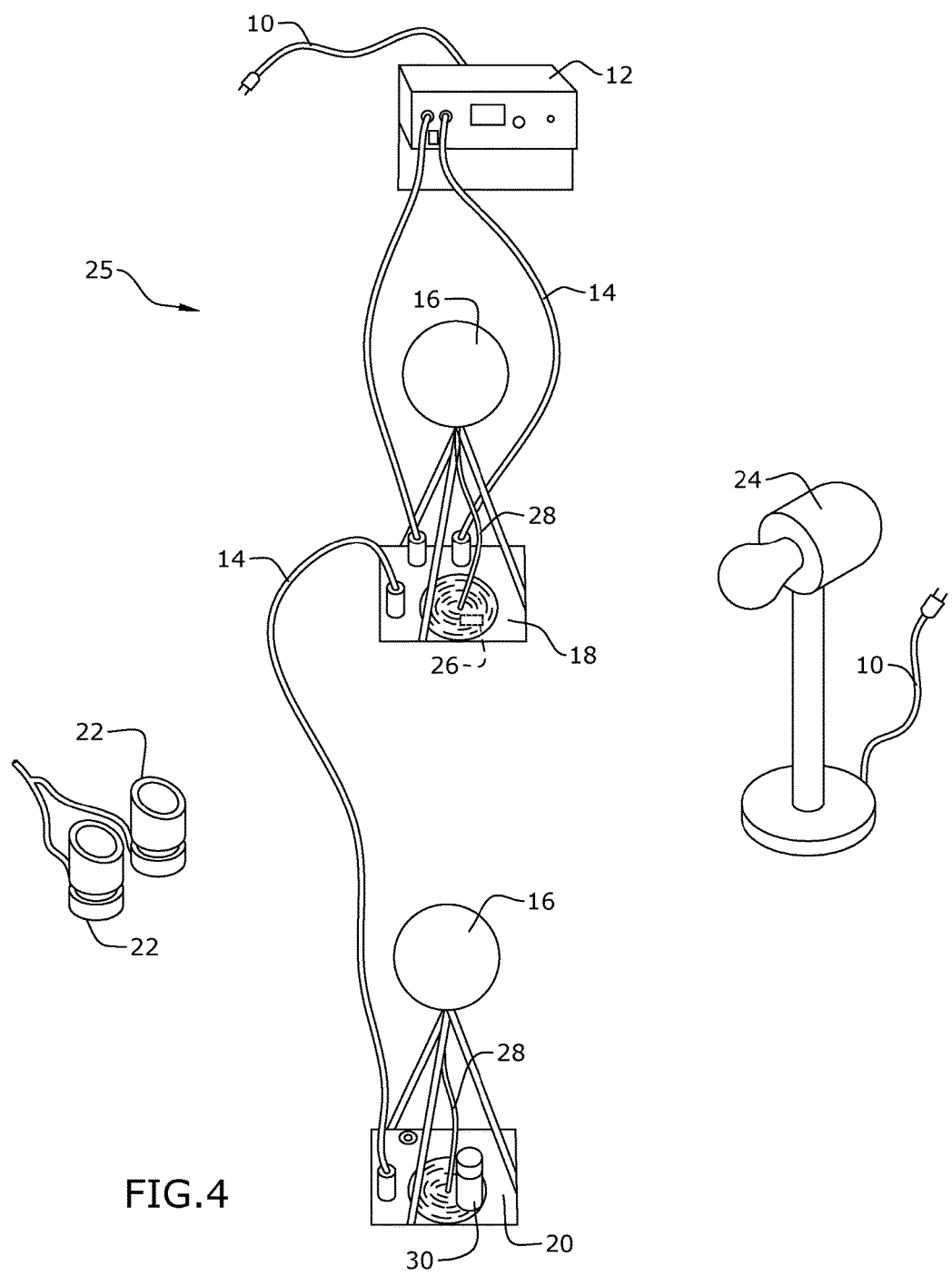
FIG. 4 is a perspective view of a system setup for programming a chip for transdermal emission of energy in accordance with an embodiment of the subject technology.

Referring now to FIGS. 3 and 4, an exemplary a system 25 setup for programming a chip according to an exemplary embodiment of the subject technology is shown. In general, a transmitting pancake coil 18 (sometimes referred to as a Tesla coil) is electrically connected to a receiver pancake coil 20. The transmitting pancake coil 18 and receiver pancake coil 20 may be separated by a predetermined distance (for example, 3 feet) and each may be connected to a respective spherical electrode 16 separated by approximately the same distance. A programmable object 26, for example, a chip may be positioned in proximity to (or in contact with) the transmitting pancake coil 18. It will be understood that the proximity to the transmitting pancake coil 18 may be based on the magnitude of the field generated by the coil 18. The programmable object 26 may be any object that can be modified by a longitudinal (scalar) charge or a longitudinal (scalar) wave/field. For sake of illustration, the programmable object 26 will be referred to herein as the hologram chip 26. The hologram chip 26 may include a chip body with a holographic layer containing a hologram. While the following description is primarily disclosed in the context of a hologram/holographic layer, it will be understood that other materials may be programmable, which may depend on the application of use. For example, in some embodiments, a layer of carbon fiber may be used in lieu of or in conjunction with a holographic layer. The programmed layer, for example, the hologram may emit and/or augment energetic frequencies/information through transdermal means. The hologram may be programmed to the natural frequencies/information of a tuning medium 30 positioned in contact with the receiver pancake coil 20. The tuning medium 30 may be any single or combination of a solid, liquid, gas, or plasma. In the example shown, liquid melatonin is a tuning medium 30 whose natural frequencies/information may be programmed into the hologram so that the frequencies/information may be turned into an energetic signal which can be transmitted transdermally from the chip to the user. The information carried by the natural frequencies/information of melatonin may thus interact with a portion of the body affecting certain functions.

To tune the chip 26, an exemplary method generates and augments longitudinal waves/field to carry the information from the tuning medium 30 to the chip 26. A power source 10 may power a wave function generator 12 (for example a direct digital synthesis function generator) to produce wave signals. The wave function generator 12 may be tuned so the waves are in resonance. This can be achieved with a sine wave at an output amplitude of approximately 8 $V_{PP}$ (Volts peak to peak) and a frequency of around 6 MHz (megahertz). Longitudinal waves may be produced in a field between the spherical electrodes 16. Energy from the receiving side spherical electrode 16 passing through the tuning medium 30 on the receiver pancake coil 20 may modulate the carrier longitudinal waves/fields to transfer the natural frequencies/information of the tuning medium 30 to the wave signals once the waves become in resonance. As shown, wiring 14 may electrically couple the power source 10 to the wave function generator 12, the wave function generator 12 to the transmitter pancake coil 18, and the transmitter pancake coil 18 to the receiver pancake coil 20.

In some embodiments, a sound source 22 and light source 24 may be included to augment/modulate the carrier longitudinal waves. In an exemplary embodiment, the sound source 22 may produce sound waves at variable frequencies. The sound source 22 may be positioned approximately three feet perpendicular to the middle of the line created by the transmitter pancake coil 18 and receiver pancake coil 20. The light source 24 may produce light waves at variable frequencies on the opposite side of the sound source 22. The light source 24 may be positioned approximately three feet perpendicular to the middle of the line created by the transmitter pancake coil 18 and receiver pancake coil 20. The sound source 22 may be tuned to a frequency of approximately 20 Hertz. The light source 24 may be tuned to a frequency of approximately 20 Hertz. The sound and light waves produced may augment/modulate the carrier longitudinal (scalar) waves/fields to transfer additional specific information and/or messages. The light and sound waves directly affect the longitudinal waves by influencing both the longitudinal waves/field as well as the receiving/transmitting coils. The light and sound do not necessarily change the information the melatonin is sending to the chip 26 but may only add to information associated with the melatonin. If the frequencies for melatonin (or another tuning medium 30) were known then they can be played through the speakers and light to add more information into the chip 26. In an exemplary embodiment, the system may run for approximately thirty minutes for the hologram to be transformed with the information transferred by the longitudinal waves.

The following discloses exemplary embodiments of the subject technology incorporated into various articles of manufacturer that may provide physiological benefits to end users. The chip 26 may ne conveniently worn or attached to various articles so that the information programmed into the chip 26 may be transferred to the user and/or to the article to which it is attached. The benefits of the hologram chip 26 have been tested on human subjects to compare the physiological effects of using the chip 26 to performance without the chip 26.

Table 1 below shows testing data of physiological effects on users before and after wearing an article with the hologram chip 26. The test measured blood flow through the posterior tibial artery (PTA) of various individuals. As can be seen, with the exception of one data point, there was a significant improvement in the blood flow through the PTA of each test subject after having worn the article with the hologram chip 26.

Figure 5:
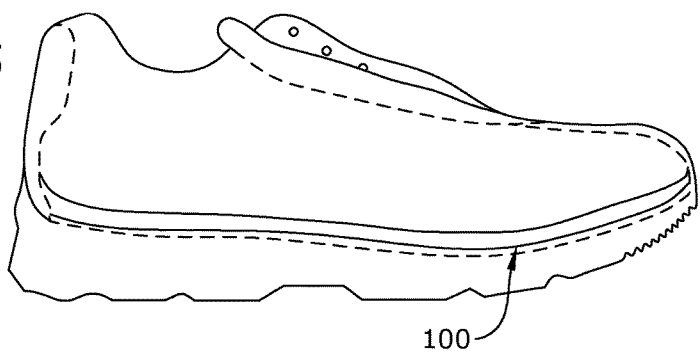
FIG. 5 is a cross-sectional side view of a shoe incorporating an insole including a programmed chip of FIG. 4 in accordance with an embodiment of the subject technology.
Figure 5A:
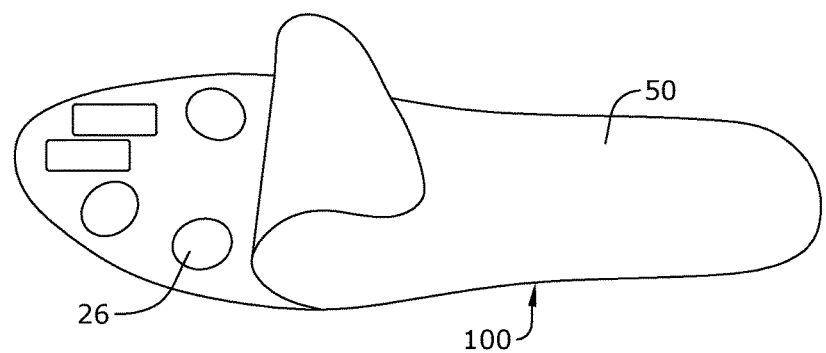
FIG. 5A is a perspective top view of an insole of FIG. 5.
Figure 5B:
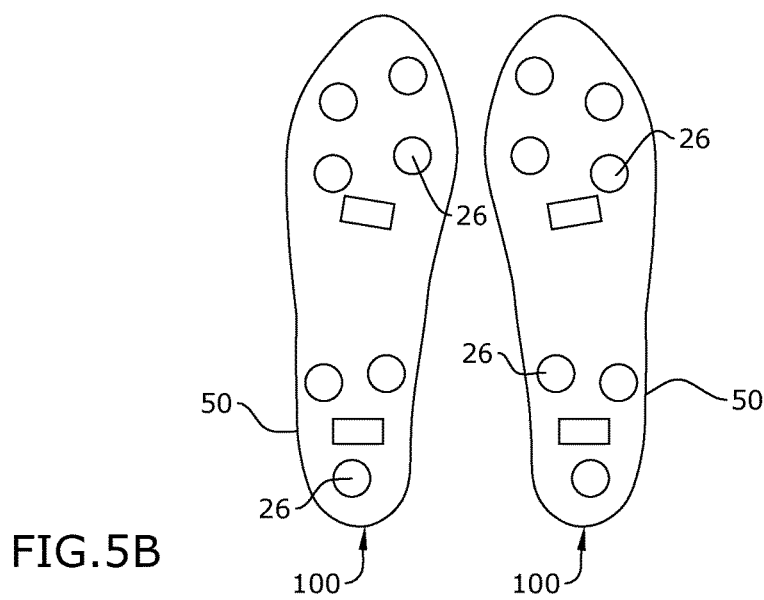
FIG. 5B is a top view of a plurality of programmed chips of FIG. 4 attached to a pair of insole inserts in accordance with an embodiment of the subject technology.

Referring now to FIGS. 5, 5A, and 5B a system 100 for transdermal emission and/or augmentation of energy to a user is shown according to an exemplary embodiment of the subject technology. The system 100 includes the hologram chip 26 attached to a fabric body 50. The fabric body 50 may be an article of apparel so that the chip 26 is in close proximity to the human body for transdermal emission and/or augmentation of information stored within the chip 26. An excellent consumer product that would benefit the user is a shoe incorporating the chip 26. A shoe provides the means to carry chip 26 in close and constant proximity to the user's dermis. As may be further appreciated, the sole of the foot is considered by many holistic practitioners to be an important interface to the health of the human body. In some embodiments, the chip 26 may be positioned in alignment with reflexology points, acupuncture points and meridian pathways. In the exemplary embodiment shown, the fabric body 50 is an insole insert with a plurality of chip 26. For example, the chip 26 may be positioned to optimize coverage with the foot. In some embodiments, chip 26 may be positioned on an exterior surface of the fabric body 50 for

TABLE 1

| Test Subject | Height | Weight (LBs) | Age | PTA Pre-Right | PTA Pre-Left | PTA Immediately After (Right) | PTA Immediately After (Left) | PTA Variance (Right) (%) | PTA Variance (Left) (%) |
|---|---|---|---|---|---|---|---|---|---|
| Female Risk Management | 5'11" | 170 | 50 | 66 | 59 | 70 | 71 | 6 | 17 |
| Male ER Nurse/Firefighter | 6'4" | 210 | 46 | 69 | 65 | 81 | 80 | 15 | 19 |
| Female Registered Nurse | N/A | N/A | N/A | 61 | 52 | 71 | 56 | 14 | 7 |
| Male Radiology Technician | 5'10" | 200 | 42 | 69 | 87 | 85 | 89 | 19 | 2 |
| Male Corporate Risk Management | 6'5" | 290 | 48 | 69 | 67 | 68 | 79 | (-) 1 | 15 |
| Female Respiratory Therapist | 5'7" | 174 | 56 | 43 | 45 | 75 | 51 | 43 | 12 |

Table 2 below shows additional test results from an individual before wearing an article with the hologram chip 26 and after wearing the hologram chip 26. The test subject performed various exercises and weight resistance for each side (if applicable) was measured. The test data shows strength improvement in exercises as measured by increased weight resistance capacity as a correlation of having worn the hologram chip 26.

direct contact with skin of the user. In some embodiments the chip 26 may line the interior of two pieces of fabric bodies 50. Ultrasound Doppler testing of blood flow to feet has shown an instant increase of approximately 14% when the feet are in contact with enhanced footwear or insoles using the subject technology. Longer use has shown even higher blood flow increase.

TABLE 2

| | Previous Exam | | | | Current | | | Change | |
|---|---|---|---|---|---|---|---|---|---|
| | Date | Left | Right | Diff | Left | Right | Diff | Left | Right |
| Neck/Trunk Recent Change | | | | | | | | | |
| Trunk Flexion | Jun. 16, 2015 | 56.7 lbs. | | — | 63.0 lbs. | | — | 11% | |
| Upper Extremity Recent Change | | | | | | | | | |
| Shoulder Flexion | Jun. 16, 2015 | 11.4 lbs. | 12.5 lbs. | −9% L | 15.2 lbs. | 14.2 lbs. | −7% R | 34% | 14% |
| Lower Extremity Recent Change | | | | | | | | | |
| Knee Extension | Jun. 16, 2015 | 32.5 lbs. | 32.3 lbs. | −1% R | 43.6 lbs. | 47.3 lbs. | −8% L | 34% | 46% |

Referring now to FIGS. 6A and 6B, a system 200 for transdermal emission and/or augmentation of energy to a user is shown according to an exemplary embodiment of the subject technology. The system 200 includes the chip 26 attached to a fabric body 210. The chip 26 may include a flexible body that may curve with the natural curvature of human body parts. In an exemplary embodiment, the fabric body 210 is an adhesive bandage including adhesive sections 215. In an exemplary embodiment, chip 26 is positioned intermediate the adhesive sections 215 so that in use, the chip 26 is positioned over a selected area of skin and the adhesive sections 215 secure the fabric body 210 to the surrounding skin. As may be appreciated, aspects of the system 200 may be useful on fingers or other round body parts (shins, arms, etc.) in which chip 26 may bend and remain in contact with the rounded body surface. Some embodiments may include a layer of medicated fluid 250 applied over chip 26. In use, the layer of medicated fluid 250 interacts with the transmitted and/or augmented information from chip 26 to augment healing. For example, the layer of medicated fluid 250 may be an adhesive, gel, or ointment. The system 200 may be applied to an injured area (for example, a cut or burn) so that the chip 26 and medicated fluid 250 may interact with the injury to stimulate body tissue and accelerate healing.

Referring now to FIG. 6C, a system 300 for transdermal emission and/or augmentation of energy to a user is shown according to an exemplary embodiment of the subject technology. The system 300 is similar to the system 200 except that the fabric body 310 is a wrappable bandage or gauze. As shown, the chip 26 is exposed however it will be understood that the chip 26 may be covered by another layer of bandaging/gauze. Some embodiments may include the medicated fluid 250 (on an underside of chip 26 so that the medicated fluid 250 may be absorbed through the fabric body 310 into contact the underlying skin. In the embodiment shown, the system 300 may be useful for treating a wrist sprain or similar soft tissue damage.

Referring now to FIG. 6D, a system 400 for transdermal emission and/or augmentation of energy to a user is shown according to an exemplary embodiment of the subject technology. The system 400 may be useful for treating large area topical ailments. The system 400 is similar to the system 300 except that the fabric body 310 includes an array 425 of chips 26 to provide a wider area of coverage. The chips 26 may be attached on the fabric body 315 so that the fabric body 315 is between the underlying skin and the chip 26 for indirect contact with the skin. Another layer of the fabric body 315 may be wrapped around the chips 26. As shown, the array 425 is partially covered on the right and left sides of the array and the array 425 is exposed for sake of illustration.

Referring now to FIG. 7, a chip 500 for transdermal emission and/or augmentation of energy to a user is shown according to an exemplary embodiment of the subject technology. As discussed above with reference to FIGS. 5, 5A, and 5B, use of the chip 26 to interface with the sole of one's foot may provide strategic access to physiological conduits of the human body. The chip 500 may be sized and shaped to mimic an insole so that it may be inserted within a shoe (for example as shown in FIG. 5). The chip 500 is programmed in the same manner as the chip 26 and as may be appreciated, covers a greater area of a person's sole thus providing increased effect on the person. In some embodiments, the chip 500 may be used in combination with a gel or other fluid medium to augment the information transmitted to the user. As a potential product, the chip 500 may be convenient for sale as a shoe accessory or as part of a shoe system.

Figure 9:
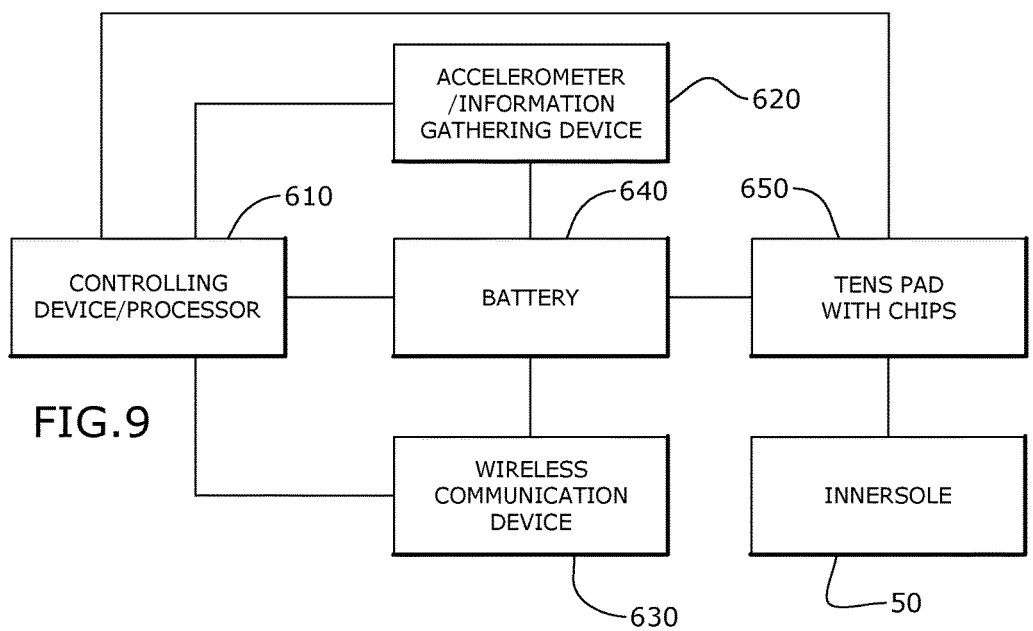
FIG. 9 is a block diagram of a system integrating the programmed chips for transdermal emission of energy and transcutaneous electrical nerve stimulation units onto an insole of FIG. 8 in accordance with an embodiment of the subject technology.

Referring now to FIGS. 8 and 9, a system 600 of an exemplary embodiment is shown which includes the system 100 (fabric body 50 in the form of an insole insert along with the programmed chip 26 and transcutaneous electrical nerve stimulation (TENS) pads 650 coupled to the insole body 50. FIG. 9 shows additional elements which may not be visible in the embodiment shown in FIG. 8. For example, a controller/processor 610 may be connected to the TENS pads 650, to an accelerometer/tracker 620, to a wireless transceiver 630, and to a power source 640. The programmed chip 26 may be used in conjunction with electric, magnetic and/or electromagnetic fields/waves generated by the TENS pads 650 to amplify or enhance the effects on the person by the chip(s) 26. The accelerometer/tracker 620 may be programmed to track a user's performance. For example, a user may track performance (speed, exercise longevity, etc.) which may be transmitted in some embodiments by the wireless transceiver 630. In another example, the TENS pads 650 may be toggled on/off and the amplified effects of the TENS pads 650 in conjunction with the chip(s) 26 may be measured.

Figure 10:
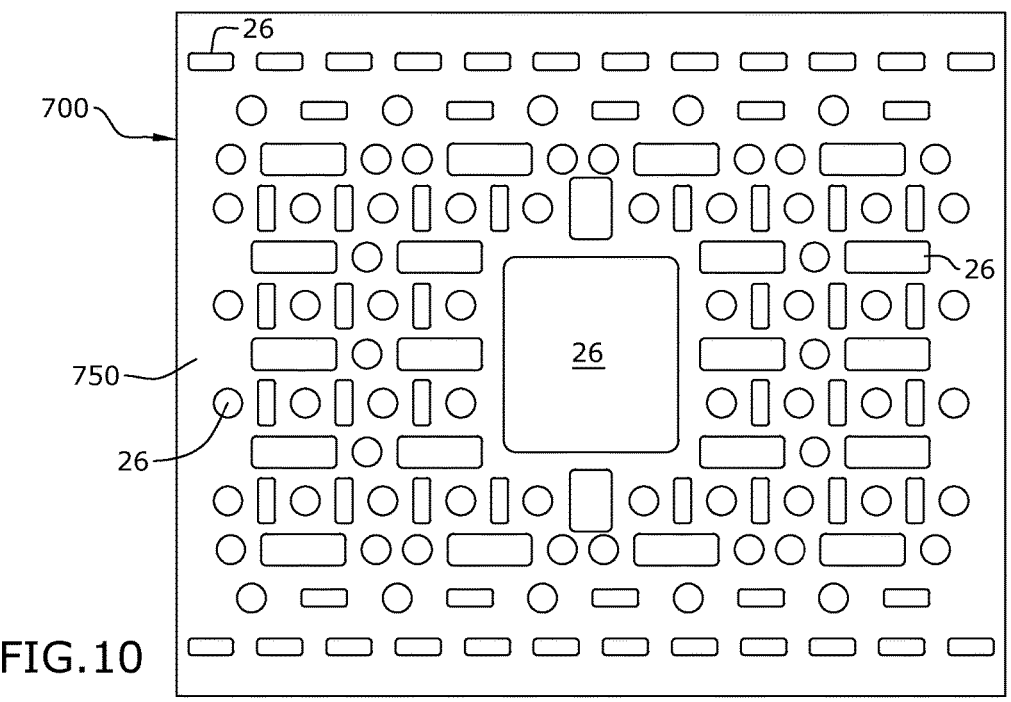
FIG. 10 is a top view of a vibration mat including an array of programmed chips in accordance with an embodiment of the subject technology.

Referring now to FIG. 10, a system 700 of an exemplary embodiment is shown which includes a plurality of the programmed chips 26 coupled to a vibration mat 750. For sake of illustration, the underlying and mechanical features of the vibration mat 750 are omitted and will be understood to comprise elements of a vibration mat as is known in the art. For example, some embodiments may affix the vibration may 750 surface to a vibration plate (not shown) or to a vibrating/frequency generating device (not shown). In an exemplary embodiment, the programmed 26 may individually be programmed (represented by chips 26 of varying shapes and sizes) to provide different effects on the user. Thus one vibration mat 750 may be configured to provide, for example, different effects to the end user.

Referring now to FIGS. 11A and 11B, a system 800 of an exemplary embodiment is shown which includes a programmed chip 26 coupled to a mobile electronic device 850. Many consumer electronic devices emit EMF that has been found in several studies to have a deleterious effect on the human body. The chip 26 may be programmed to offset the negative effects of EMF output from the mobile electronic device 850, which may be for example a smart phone, tablet, transponder, or GPS enabled device which users may frequently carry and/or put up to their head. For example, the EMF output may promote cancerous growth in body tissue. The incorporation of the chip 26 to the mobile electronic device 850 may promote healthy interaction with tissue simultaneously to the same area EMF output is affecting.

Referring now to FIG. 12, a system 900 of an exemplary embodiment is shown which includes a programmed chip 26 coupled to a container 950. The container 950 may be for example a bottle holding water or other liquid/beverage. The programmed chip 26 may transfer programmed information into the liquid to be consumed. The liquid may thus be a carrier of the programmed information that can be ingested internally so that the positive effects of the chip 26 may be carried through the circulatory system.

Persons of ordinary skill in the art may appreciate that numerous design configurations may be possible to enjoy the functional benefits of the inventive systems. Thus, given the wide variety of configurations and arrangements of embodiments of the present invention the scope of the present invention is reflected by the breadth of the claims below rather than narrowed by the embodiments described above. For example, many other articles of manufacture may incorporate the programmed chip 26 providing positive health benefits as described above. While shoes were described as one excellent product carrying the chip 26, other pieces of clothing are likewise contemplated. In addition, other apparel or accessories (for example eye wear, jewelry, etc.) may incorporate the chip 26 with similarly expected results and are contemplated herein.

What is claimed is:

1. A device for emission of energy, comprising:
   a substrate; and
   a programmable layer of the substrate, wherein:
      the programmable layer is programmed with longitudinal electromagnetic scalar waves passed through a tuning medium apart from the substrate,
      the longitudinal electromagnetic scalar waves having an amplitude of the waveform change to modulate desired information onto a carrier wave,
      electromagnetic waves in the form of light and/or sound are used to modulate the carrier wave as it programs the substrate at either one or any combination of receiving and transmitting pancake coils, and
      the programmable layer is configured to emit and/or augment energetic information from the substrate, tuned via the longitudinal electromagnetic scalar waves, the energetic information being tuned for interaction with a human body.

2. The device of claim 1, wherein the energetic information is based on a natural frequency of the tuning medium.

3. The device of claim 1, wherein the programmable layer is a holographic layer.

4. The device of claim 1, wherein the programmable layer comprises carbon fiber.

5. The device of claim 1, wherein the energetic information emitted from the programmable layer is programmed to offset negative effects of electromagnetic field (EMF) output from a mobile electronic device when the device is in proximity of the mobile electronic device.

6. The device of claim 5, wherein the mobile electronic device is any electromotive force (EMF) emitting device.

* * * * *